US008142772B2

(12) United States Patent
Noessner et al.

(10) Patent No.: US 8,142,772 B2
(45) Date of Patent: Mar. 27, 2012

(54) ATTACK OF TUMOR CELLS WITH MISSING, LOW OR ABERRANT MHC EXPRESSION BY COMBINING NON MHC-RESTRICTED T-CELLS/NK-CELLS AND MHC-RESTRICTED CELLS

(75) Inventors: Elfriede Noessner, Munich (DE); Elisabeth Weiss, Munich (DE); Dolores Schendel, Munich (DE); Christine Falk, Munich (DE)

(73) Assignee: Helmholtz Zentrum Munchen Deutsches Forschungszentrum fur Gesundheit und Umwelt (GmbH), Neuherberg (DE)

( * ) Notice: Subject to any disclaimer, the term of this patent is extended or adjusted under 35 U.S.C. 154(b) by 0 days.

(21) Appl. No.: 12/765,234

(22) Filed: Apr. 22, 2010

(65) Prior Publication Data

US 2010/0203086 A1 Aug. 12, 2010

Related U.S. Application Data

(63) Continuation of application No. 10/190,281, filed on Jul. 5, 2002, now Pat. No. 7,731,950.

(30) Foreign Application Priority Data

Jul. 5, 2001 (DE) .................................. 101 32 502

(51) Int. Cl.
*A01N 63/02* (2006.01)
*A61K 48/00* (2006.01)
*A61K 39/00* (2006.01)
(52) U.S. Cl. ................. 424/93.21; 424/93.3; 424/93.71; 424/184.1; 424/277.1
(58) Field of Classification Search .................. None
See application file for complete search history.

(56) References Cited

U.S. PATENT DOCUMENTS

| | | | |
|---|---|---|---|
| 4,415,553 A | 11/1983 | Zhabilov et al. | |
| 4,568,542 A | 2/1986 | Kronenberg | |
| 4,789,658 A | 12/1988 | Yoshimoto et al. | |
| 4,877,611 A | 10/1989 | Cantrell | |
| 5,156,841 A | 10/1992 | Rapp | |
| 5,229,115 A | 7/1993 | Lynch | |
| 5,290,551 A | 3/1994 | Berd | |
| 5,582,831 A | 12/1996 | Shinitzky | |
| 5,591,430 A * | 1/1997 | Townsend et al. | 424/93.71 |
| 6,261,839 B1 | 7/2001 | Multhoff et al. | |
| 6,849,452 B1 | 2/2005 | Zitvogel et al. | |
| 7,731,950 B2 | 6/2010 | Noessner et al. | |
| 2001/0012632 A1 | 8/2001 | Moser et al. | |
| 2002/0177551 A1 | 11/2002 | Terman | |

FOREIGN PATENT DOCUMENTS

| | | |
|---|---|---|
| EP | 1 275 400 B1 | 11/2004 |
| EP | 1 932 537 A1 | 6/2008 |
| FR | 2 775 692 A1 | 9/1999 |
| WO | WO97/29182 | 8/1997 |
| WO | WO98/48630 | 11/1998 |
| WO | WO 01/41788 * | 6/2001 |

OTHER PUBLICATIONS

Kos and Engleman (Journal of Immunology, 1995, vol. 155, pop. 578-584).*
Kos and Engleman (Immunology Today, 1996, vol. 174, pp. 1-3).*
Veelken et al (International Journal of Cancer, 1997, vol. 70, pp. 269-277).*
Kale (European Journal of Immunology, 1990, vol. 20, pp. 369-377).*
Schendel et al (Journal of Molecular Medicine, 1997, vol. 75, pp. 400-413).*
Gupta et al (Human Gene Therapy, 1997, vol. 8, pp. 1701-1714).*
Grimm et al (Journal of Experimental Medicine, 1982, vol. 155, pp. 1823-1841).*
Abe et al., Lymphotcine Cytokine Res. Medline. vol. 12, No. 5 pp. 279-283 (1993).
Bachman et al., Journal of Immunology. vol. 175 pp. 4677-4685 (2005).
Baxeranis et al., Lancer Immunology, Immunotherapy. Medline. vol. 40, No. 6 pp. 410-418 (1995).
Berg et al., Sustained TCR Signaling is Required for Mitogen-Activated Protein Kinas Activation and Degranulation by Cytotoxic T Lymphocytes. The Journal of Immunology. vol. 161 pp. 2919-2924 (1998).
Bignon et al., "HLA DNA class II typing by PCR-SSOP: 12th International Histocompatibility Workshop experience," In: Charron D, editor. HLA: Genetic diversity of HLA. Functional and medical Implication. EDK Medical and Scientific International Publisher, 1997: 21-25.
Braud et al., "HLA-E binds to natural killer cell receptors CD94/NKG2A, B and C," Letters to Nature. vol. 391 pp. 795-799 (1998).
Browning et al., "The HLA-A,B,C genotype of the class I negative cell line Daudi reveals novel HLA-A and -B alleles," Tissue Antigens. vol. 45 pp. 177-187 (1995).
Bukowski, "Natural History and Therapy of Metastic Renal Cell Carcinoma," Cancer. vol. 80 pp. 1198-1220 (1997).
Cabrera et al., "High Frequency of Altered HLA Class I Phenotypes in Invasive Breast Carcinomas," Human Immunology. vol. 50 pp. 127-134 (1996).
Cabrera et al., "High Frequency of Altered HLA Class I Phenotypes in Laryngeal Carcinomas," Human Immunology. vol. 61 pp. 499-506 (2000).
Carreno, B.M., and Collins, M., "The B7 Family of Ligands and Its Receptors: New Pathways for Costimulation and Inhibition of Immune Respones," Annu. Rev. Immunol. vol. 20 pp. 29-53 (2002).

(Continued)

*Primary Examiner* — Karen Canella
(74) *Attorney, Agent, or Firm* — Jenkins, Wilson, Taylor & Hunt, P.A.

(57) ABSTRACT

This invention is directed to therapeutic compositions containing non-MHC-restricted Tcells/NK-cells in combination with MHC-restricted T-cells and especially to therapeutic compositions, which comprise LAK cells. Furthermore, the present invention is directed to the use of the above combination in the treatment of tumors in humans, which tumors show a missing, low or aberrant expression of MHC class Ia or Ib molecules. By using the aforementioned compositions/combinations it is possible to provide a balanced selective pressure against emergence of tumor cell variants that would otherwise escape immune detection.

20 Claims, 5 Drawing Sheets

OTHER PUBLICATIONS

Cesano et al., Journal of Clinical Investigation. vol. 94 pp. 1076-1084 (1994).
Chen et al., "Induction of Antitumor Immunity with Combination of HER2/neu DNA Vaccine and Interleukin 2 Gene-modified Tumor Vaccine," Clinical Cancer Research. vol. 6 pp. 4381-4388 (2000).
Colonna et al., "A high-resolution view of NK-cell receptors: structure and function," Trends Immunology Today. vol. 21, No. 9 pp. 428-431 (2000).
Cruse et al., Immunol. Immunophermacol. Lifesci. vol. 9, No. 2 pp. 41-53 (1989).
Efferson et al., Anticancer Research. vol. 25 pp. 715-724 (2005).
European Search Report corresponding to European Patent Application No. 02015101.5-2107 dated Nov. 11, 2002.
Fabre, J.W., "The allogenic response and tumor immunity," Nature Medicine. vol. 7, No. 6 pp. 649-652 (2001).
Falk et al., Retaliation against Tumor Cells Showing Aberrant HLA Expression Using Lymphokine Activated Killer-derived T Cells. Cancer Research. vol. 62 pp. 480-487 (2002).
Finke et al., Immunolgy Today. vol. 20 pp. 158-160 (1999).
G.P. Leong, Surgical Clinical of North America. Medline. vol. 76, No. 6 pp. 1355-1381 (1996).
Gastl et al., "Retroviral Vector-mediated Lymphokine Gene Transfer into Human Renal Cancer Cells," Cancer Research. vol. 52 pp. 6229-6236 (1992).
Giacomini et al. "HLA-C heavy chains free of (2-microglobulin: distribution in normal tissues and neoplastic lesions of non-lmyphoid origin and interferon-γ responsiveness," Tissue Antigens. vol. 50 pp. 555-566 (1997).
Grewal, I.S., and Flavell, R.A., "CD40 and CD154 in Cell-Mediated Immunity," Annual Review of Immunolgy. vol. 16 pp. 111-135 (1998).
Ho et al., "Costimulation of Multiple NK Cell Activation Receptors by NKG2D," The Journal of Immunolgoy. vol. 169 pp. 3667-3675 (2002).
Hoffman et al., Adoptive Cellular Therapy. Seminars in Oncology. vol. 27, No. 2 pp. 221-233 (2000).
Jabrane-Ferrat et al., "Recombinant gamma interferon provokes resistance of human breast cancer cells to spontaneous and IL-2 activated non-MHC restricted cytotoxicity," Br. J. Cancer. vol. 61 pp. 558-562 (1990).
Jäger et al., "Clinical cancer vaccine trials," Current Opinion in Immunology. vol. 14 pp. 178-182 (2002).
Jager et al., Mini Review: Antigen-Specific Immunotherapy and Cancer Vaccines. Int. J. Cancer. vol. 106 pp 817-820 (2003).
Janeway et al., Immunobiology: the immune system in health and disease. 6th Edition. Garland Science Publishing. p. 94 (2005).
Jayson et al., "A randomized phase II trial of interleukin 2 and interleukin 2-interferon alpha in advanced renal cancer," British Journal of Cancer. vol. 78, No. 3 pp. 366-369 (1998).
Jonasch, E., and Haluska, F.G., "Interferon in Oncological Practice: Review of Interfereon Biology, Clinical Applications, and Toxicities," The Oncologist. vol. 6 pp. 34-55 (2001).
Kruit et al., "High-Dose Regimen of Interleukini-2 and Interfereon-Alpha in Combination with Lymphokine-Activated Killer Cells in Patients with Metastatic Renal Cell Cancer," Journal of Immunotherapy. vol. 20, No. 4 pp. 312-320 (1997).
Kruit et al., "The role of possible risk factors for acute and late renal dysfunction after high-dose itnerleukin-2, interfereon ( and lymphokine-activated killer cells," Cancer Immunol. Immunother. vol. 48 pp. 331-335 (1999).
Lardy and Doxiadis, "One dimensional iso-electric focusing (1D-IEF) of HLA class I variants: 12th International Histocompatibility Workshop experience," In: Charron D, editor. HLA: Genetic diversity of HLA. Functional and medical Implication. EDK Medical and Scientific International Publisher, pp. 18-20 (1997).
Law et al., "Phase II Randomized Trial of Interleukin-2 with or without Lymphokine-Activated Killer Cells in the Treatment of Patients with Advanced Renal Cell Carcinoma," Cancer. vol. 76, No. 5 pp. 824-832 (1995).
Ledbetter et al., Stimulation of T Cells through the CD2/T-Cell Receptor Complex: Role of Cytoplasmic Calcium, Protein Kinase C Translocation, and Phosphorylation of pp60c-src in the Activation Pathway. Molecular and Celluular Biology, vol. 7, No. 2 pp. 650-656 (1987).
Long, "Regulation of Immune Responses Through Inhibitory Receptors," Annual Review of Immunology. vol. 17 pp. 875-904 (1999).
López-Botet et al., "Paired Inhibitory and Triggering NK Cell Receptors for HLA Class I Molecules," Human Immunology. vol. 61 pp. 7-17 (2000).
Maier et al., "Implication of HLA-E Allele Expression and Different HLA-E Ligand Diversity of the Regulation of NK Cells," Human Immunology. vol. 61 pp. 1059-1065 (2000).
Malek, T.R., and Bayer, A.L., Tolerance, Not Immunity, Crucially Depends on IL-2. Nature Reviews. vol. 4 pp. 665-674 (2004).
Manger et al., The Role of Protein Kinase C in Transmembrane Signaling by the T Cell Antigen Receptor Complex. The Journal of Immunology. vol. 139, No. 8 pp. 2755-2760 (1987).
Melief et al., Res. Immunol. Medline. vol. 142, No. 5-6 pp. 425-429 (1991).
Multhoff, G., Heat shock proteins in immunity. vol. 172 pp. 279-304 (2006) [Abstract].
Negrier et al., "Recombinant Human Interleukin-2, Recombinant Human Interferon Alfa-2a, or Both in Metastatic Renal-Cell Carcinoma," The New England Journal of Medicine. vol. 338 pp. 1272-1278 (1998).
Norgaard et al., "A mRNA based SBT protocol for typing of HLA-A locus alleles," In Charron D, editor. HLA: Genetic diversity of HLA. Functional and medical Implication. EDK Medical and Scientific International Publisher, pp. 254-257 (1997).
Official Action corresponding to U.S. Appl. No. 10/190,281 dated Oct. 12, 2005.
Official Action corresponding to U.S. Appl. No. 10/190,281 dated Mar. 15, 2006.
Official Action corresponding to U.S. Appl. No. 10/190,281 dated Oct. 16, 2006.
Official Action corresponding to U.S. Appl. No. 10/190,281 dated Mar. 7, 2007.
Official Action corresponding to U.S. Appl. No. 10/190,281 dated Sep. 24, 2007.
Official Action corresponding to U.S. Appl. No. 10/190,281 dated Jul. 9, 2008.
Official Action corresponding to U.S. Appl. No. 10/190,281 dated Aug. 4, 2009.
Parmiani, An explanation of the variable clinical response to interleukin 2 and LAK cells. Immunology Today. Elsevier Science Publishers Ltd. (UK), vol. 11, No. 4 pp. 113-115 (1990).
Pittet et al., Cutting Edge: Cytolytic Effector Function in Human Circulating CD8+ T Cells Closely Correlates with CD56 Surface Expression. The Journal of Immunology. vol 164 pp. 1148-1152 (2000).
Radons and Multhoff, Immunostiumulatory functions of membrane-bound and exported heat shock protein 70. Exerc. Immunol. Rev. vol. 11 pp. 17-33 (2005) [Abstract].
Ravetch, J.V., and Lanier, L.L., "Immune Inhibitory Receptors," Science. vol. 290 pp. 84-89 (2000).
Rosenberg et al., "Observation on the Systemic Administration of Autologous Lymphokine-Activated Killer Cells and Recombinant Interleukin-2 to Patients with Metastatic Cancer," The New England Journal of Medicine. vol. 313, No. 23 pp. 1485-1492 (1985).
Rosenberg et al., "Prospective Randomized Trial of High-Dose Interleukin-2 Alone or in Conjuction With Lymphokine-Activated Killer Cells for the Treatment of Patients With Advanced Cancer," Journal of the National Cancer Institute. vol. 85, No. 8 pp. 622-632 (1993).
Rosenberg, "Adoptive Immunotherapy of Cancer Using Lymphokine Activated Killer Cells and Recombinant Interleukin-2," Important Adv. Oncol. pp. 55-91 (1986).
Rosenberg, "Interleukin-2 and the Development of Immunotherapy for the Treatment of Patients with Cancer," The Cancer Journal from Scientific American. vol. 6, Supplement 1. pp. S2-S7 (2000).
Rosenberg, "Lymphokine-Activated Killer Cells: A New Approach to Immunotherapy of Cancer," JNCI. vol. 75, No. 4 pp. 595-603 (1985).

Schendel et al., "Gene transfer of human interferon gamma complementary DNA into a renal cell carcinoma line enhances MHC-restricted cytotoxic T lymphocyte recognition but suppresses non-MHC-restricted effector cell activity," Gene Therapy. vol. 7 pp. 950-959 (2000).

Schendel et al., "Human CD8+ T lymphocytes," In: Levkovits I, editor. the Immunology methods Manual. London: Academic Press, pp. 669-690 (1997).

Schendel et al., "Standardization of the Human in vitro Cell-mediated Lympholysis Technique," Tissue Antigens. vol. 13 pp. 112-120 (1979).

Schendel et al., "Tumor-specific lysis of human renal cell carcinomas by tumor-infiltrating lymphocytes. I. HLA-A2-restricted recognition of autologous and allogenic tumor lines," The Journal of Immunology. vol. 151 pp. 4209-4220 (1993).

Schendel et al., Cancer Research. vol. 53 pp. 4020-4025 (1993).

Schendel et al., Mol. Med. Medline. vol. 75, No. 6 pp. 400-413 (1997).

Schlesbusch et al., Hybridoma. Medline. vol. 14, No. 2 pp. 167-174 (1995).

Schleypen et al., Cytotoxic Markers and Frequency Predict Functional Capacity of Natural Killer Cells Infiltrating Renal Cell Carcinoma. Human Cancer Biology. vol. 12, No. 3 pp. 718-725 (2006).

Schmitz et al., "An IL-2-Dependent Switch Between CD95 Signaling Pathways Sensitizes Primary Human T Cells Toward CD95-Mediated Activation-Induced Cell Death," The Journal of Immunology. vol. 171 pp. 2930-2936 (2003).

Shimizu, Y., and DeMars, R., "Production of human cells expressing individual transferred HLA-A,-B,-C genes using an HLA-A,-B,-C null human cell line," The Journal of Immunology. vol. 142 pp. 3320-3328 (1989).

Stedman's Medical Dictionary, (on-line version) 2000, line 1-3.

Taniguchi et al., "Interferon induces lung colonization by intravenously inoculated B16 melonama cells in parallel with enhanced expression of class I major histocompatibility complex antigens," PNAS. vol. 84 pp. 3405-3409 (1987).

Tomita et al., "Adoptive immunotherapy of Patients with Metastatic Renal Cell Cancer Using Lumphokine-Activated Killer Cells, Interleukin-2 and Cyclophosphamide: Long-Term Results," Int. J. Urol. vol. 5 pp. 16-21 (1998).

Tongio et al., "12th International Histocompatibility Workshop HLA class I monoclonal antibodies study," In: Charron D, editor: HLA: Genetic diversity of HLA. Functional and medical Implication. Charron, D., pp. 8-12 (1997).

Uberti et al. Clinical Immunology and Immunopathology. vol. 70 pp. 234-240 (1994) [Abstract ].

Uberti et al., Preclinical Studies Using Immobilized OKT3 to Activate Human I Cells for Adoptive Immunotherapy: Optimal Conditions for the Proliferation and Induction of Non-MHC-Restricted Cytotoxicity. Clinical Immunology and Immunopathology. vol. 70, No. 3 pp. 234-240 (1994).

Wacholtz, M.C., and Lipski, P.E., Anti-CD 3-Stimulatied Ca2+ Signal in Individual Human Peripheral T Cells. The Journal of Immunology. vol. 150, No. 12 pp. 5338-5349 (1993).

Wen et al., "4-1BB Ligand-Mediated Costimulation of Human T Cells Induced CD4 and CD8 T Cell Expansion, Cytokine Production, and the Development of Cytolytic Effector Function," The Journal of Immunolgoy. vol. 168 pp. 4897-4906 (2002).

Wheeler (Salud p'ublica de M'exico, Jul.-Aug. 1997 vol. 39, No. 4 pp. 283-287 [Abstract].

Yamamoto et al., Clin. Exp. Immunol. vol. 100 pp. 13-20 (1995).

* cited by examiner ically appropriate that they recognize peptides derived from intracellular antigens that are presented by class I molecules. Moreover, since class I molecules are expressed by nearly all nucleated cells, CTL are able to recognize and destroy virtually any cell if it presents the appropriate MHC/peptide complex. On the other hand, class II molecules present peptides to CD4 positive T helper cells, the primary function of which is to secrete cytokines that promote activities of other lymphocytes, including B cells, macrophages and CTL. They play a dominant role in orchestrating an immune response.

ATTACK OF TUMOR CELLS WITH MISSING, LOW OR ABERRANT MHC EXPRESSION BY COMBINING NON MHC-RESTRICTED T-CELLS/NK-CELLS AND MHC-RESTRICTED CELLS

CROSS REFERENCE TO RELATED APPLICATIONS

This application is a continuation of U.S. patent application Ser. No. 10/190,281, filed Jul. 5, 2002 now U.S. Pat. No. 7,731,950, which itself claimed priority to German Patent Application DE 10132502.9, filed Jul. 5, 2001. The disclosure of each of these applications is incorporated by reference herein in its entirety.

TECHNICAL FIELD

This invention is directed to therapeutic compositions containing non-MHC-restricted T-cells/NK-cells in combination with MHC-restricted T-cells and especially to therapeutic compositions, which contain LAK cells. Furthermore, the present invention is directed to the use of the above compositions in the treatment of tumors in humans, which tumors show a missing, low or aberrant expression of MHC molecules.

BACKGROUND ART

Immune recognition by most T lymphocytes occurs through surface interactions involving a specific T cell receptor (TCR) on the lymphocyte and an antigen on the target cell. Unlike antibodies, TCR do not recognize intact antigens. With few exceptions, they only recognize fragments of antigens, in the form of peptides, which are presented on the cell surface by molecules of the major histocompatibility complex (MHC). The ability of T cells to recognize antigen only when it is presented by MHC molecules is called "MHC restriction". The reacting T cells are referred to as MHC-restricted lymphocytes. There are two classes of MHC molecules, class I and class II, which are functionally distinguished by the type of antigen they bind and the subset of T cells with which they interact. The dichotomy between class I and class II molecules relates to their different roles in T cell activation. Class I molecules present peptides to MHC-restricted CD8 positive cytotoxic T lymphocytes (CTL). These cells directly lyse target cells; therefore it is biolog MHC molecules are characterized by their highly polymorphic nature and many different variants have been defined which are encoded by different gene loci and alleles. Many of the amino acid variations that distinguish MHC alleles are localized in the binding groove where they modulate its shape and charge. Peptides capable of binding to a particular MHC molecule must fit to the configuration of that molecule's binding groove. Within the human population there are many different MHC alleles and an individual generally expresses six different class Ia molecules (encoded by the HLA-A, -B, -C loci), each of which binds a different repertoire of peptides due to different amino acid composition of the peptide binding groove. In addition an individual has HLA alleles encoding a number of class Ib molecules, including HLA-E, F and G.

For MHC-restricted cells to respond to antigenic stimulation, MHC/peptide complexes must be expressed at the surface of a target cell and the T cells must express a cognate TCR. The specific ability of T-cells, to recognize specific antigens, which are presented via MHC molecules, was used in a variety of therapeutical approaches, e.g. in the antitumor therapy.

However, the known strategies do not take into consideration that the immune system has a substantial repertoire of non-MHC-restricted T-cells, which might be used for the elimination of tumor cells. This is partially due to the fact that attempts to use them in the anti-tumor therapy simply were not successful. Generally, the non-MHC-restricted type of T-lymphocytes combat tumors by their recognition of tumor cells, that occurs independently of MHC-peptide ligand expression.

Examples of cells which show non-MHC-restricted immune response are Lymphokine Activated Killer (LAK) cells. They represent mixtures of activated natural killer (NK) and non-MHC-restricted T cells that lyse various tumor cells as well as HLA class I negative target cells. Activated NK cells, like those present in LAK populations, are inhibited in their cytolytic function following interaction with MHC class I molecules. Regulation of LAK-derived T (LAK-T) cells has never been clarified.

The emerging understanding of the role of negative regulation of lymphocyte function through inhibitory receptor interactions with MHC class I molecules provides new insight into mechanisms that influence LAK function. While activating receptors such as natural cytotoxicity receptors are responsible for the induction of NK-mediated lysis, the cytolytic capacity of NK cells is ultimately determined by their inhibitory receptor expression. Natural killer cells (NK) are crucial for T cell activation in the present invention. Natural killer (NK) cells are a lineage of lymphoid cells, which lacks antigen-specific receptors, and NK cells are part of the innate immune system. These cells circulate in the blood as large lymphocytes with distinctive cytotoxic granules. These lymphocyte-like cells show important functions in innate immunity. They are able to recognize and kill some abnormal cells, for example tumor cells and virus-infected cells, and are thought to be important in the innate immune defence against intracellular pathogens. Although lacking antigen-specific receptors, they can detect and attack certain virus-infected cells.

Extensive analyses of different sources of NK cells have shown that essentially all human NK cells bear inhibitory receptors that interact with class I molecules and inhibit their cytotoxicity, thereby protecting normal somatic cells from NK-mediated attack (reviewed in (1-3). Two forms of inhibitory receptors are expressed by NK cells: the killer cell inhibitory receptors (KIR) belong to the immunoglobulin superfamily and interact with classical MHC class Ia (HLA-A, -B, -C) molecules whereas inhibitory receptors of the C-type lectin superfamily are composed of CD94/NKG2A heterodimers that bind non-classical MHC class Ib (HLA-E) molecules (4; 5). Through expression of class Ia and Ib molecules, nucleated cells bear two sets of ligands that can independently prevent their attack by NK cells bearing either of these inhibitory receptor types.

However, as stated above, the regulation of LAK-derived T (LAK-T) cells has never been clarified.

In recent years, new therapeutic approaches utilizing the immune system have been investigated for treatment of tumors that can not be eliminated by current chemotherapies or radiation therapies. The first immune therapies used systematic application of Interferons, either IFNα or IFNγ, often in combination with IL-2 (6-9).

Rosenberg and colleagues were the first to explore the antitumor potential of LAK cells for immune therapy of cancer patients (10; 11). Following adoptive transfer of LAK cells into patients with advanced disease, some patients showed dramatic responses but many tumors failed to regress. Numerous animal studies and in vitro analyses of human LAK cells pinpointed activated NK cells as the major effector component mediating tumor regression, although weaker cytotoxic function was also found in the T cell fraction. However, clinical trials using LAK cells, applied either alone or in combination with high dose IL-2 to retain NK viability, failed to improve clinical efficacy. Furthermore, clinical benefits were severely limited by concurrent toxicity, particularly when IL-2 was coadministered with the LAK cells.

Further clinical trials studied the capacity of unseparated LAK cells to mediate antitumor activity in vivo following the adoptive transfer of large numbers of cells into patients with advanced disease (10; 12-20). While dramatic regression of some tumor lesions was observed, this occurred rarely, was short-lived and associated with high toxicity. In patients receiving systemic high dose IL-2 therapy, induction of LAK cells was observed in vivo and in vitro in most individuals, irrespective of their clinical responses, indicating that the efficacy of LAK cells was most likely regulated at the level of interaction between effector cells and tumor cells. The failure to identify the basis of LAK-mediated tumor regression, thereby allowing patients to be identified who might benefit from this therapy despite its associated toxicity, limited further clinical development.

This toxicity, together with the inability to understand why only some tumors regressed, led to the abandonment of non-MHC-restricted tumor cells, like LAK cells in favor of therapeutic strategies designed to adoptively transfer tumor-infiltrating lymphocytes or to induce MHC-restricted T cell responses. These newer strategies also show promise but, once again, tumor regression has only been observed in some patients. Interestingly, in several well-studied examples it was found that tumor variants emerged that showed partial or complete loss of MHC class I expression in patients who had generated strong class I-restricted CTL responses in vivo.

Thus, it appears that selective pressure by the CTL led to the emergence of tumor variants that no longer express the corresponding MHC-peptide complexes that are seen by the TCR of the CTL.

Extensive immunohistochemical studies of tumors have revealed a high prevalence of cells showing aberrant expression of HLA molecules, often limited to selected HLA allotypes. While such tumors still bind pan class I antibodies, like W6/32, their disturbed MHC expression might allow them to escape elimination by MHC-restricted CTL.

Therefore, it is the object of the present invention to provide an improved strategy for the treatment of tumors, which show a low, missing or aberrant expression of MHC class I molecules.

This problem is solved by the features set forth in the independent claims. Preferred embodiments of the present invention are detailed in the dependent claims.

The problems that are related to the therapies/compositions that have been used up to now are on the one hand due to the above described escape mechanism, which causes a reduced susceptibility of tumor cells for attack by MHC-restricted T-cells. On the other hand, as indicated above, therapies that involved non-MHC-restricted T-cells have not shown long lasting, reproducible and effective therapeutic results.

In recent experiments the inventors showed, that non MHC-restricted T-cells, e.g. LAK-T cells, like activated NK cells, are inhibited by interactions with HLA class I molecules. LAK-T cells lyse class I positive tumor cells but lysis is suppressed when tumor cells are stimulated with interferon-gamma to increase their class I expression. This inhibition of cytotoxicity is however reversed in the presence of class I-specific monoclonal antibody. HLA negative target cells can be partially protected from lysis by LAK-T cells following their transfection to express HLA class Ia or class Ib molecules. The principle of negative regulation by HLA molecules thus applies to non-MHC-restricted T-cells, such as LAK-T cells generated from tumor patients and healthy control donors. Although LAK-T cells are inhibited by class Ia and class Ib molecules, they do not express known NK inhibitory receptors. Apparently, they are negatively regulated through hitherto undefined inhibitory receptors. Experiments conducted by the inventors showed that these T-cells would be most effective in recognizing tumor cell variants that show low or disturbed MHC class I expression since their cytotoxic function could not be efficiently inhibited by interactions with class I molecules. These results have lead to a new approach, which allows an effective use of non-MHC restricted T-cells, e.g. LAK T-cells, in the therapy of tumor diseases by combating tumor variants showing low or aberrant expression of specific HLA allotypes.

Based on this research work, the use of therapeutic compositions containing immune cells, which attack tumor cells in a non-MHC-restricted way, in combination with MHC-restricted T-cells, provide a balanced selective pressure against emergence of tumor cell variants that would otherwise escape immune detection.

Generally, a therapeutic composition according to the present invention contains:
a) activated non-MHC-restricted T-cells and/or Natural Killer (NK) cells in combination with
b) MHC-restricted T-cells or
c) therapeutic agents, which induce immune responses of MHC-restricted T cells.

These ingredients may also be contained in a kit of parts comprising one or more containers filled with one or more of the ingredients of the aforementioned composition of the invention. By means of this kit it is possible to separately or simultaneously administer those ingredients.

SUMMARY

According to one preferred embodiment, Lymphokine Activated Killer (LAK) cells are used as activated non-MHC-restricted T-cells and/or Natural Killer (NK) cells.

LAK cells represent a composite population of CD3$^-$ NK cells and CD3$^+$ T cells, of both the CD4 and CD8 subsets. Characteristic of LAK cells is their capacity to lyse a variety of tumor cells in a non-MHC-restricted fashion. In addition, LAK cells can kill class I negative target cells, such as Daudi and K562, which serve as general standards for identification of non-MHC-restricted cytotoxic effector cells. Separation of LAK populations into CD3$^-$ and CD3$^+$ fractions revealed that both NK cells and T cells could lyse class I negative target cells and a variety of different tumor cells.

In practice, LAK cells show one major advantage over other non-MHC-restricted T-cells/NK cells, which is the relatively simple way, in which these cells can be produced in vitro. As described above and as it is described in detail in the Examples, LAK cells are derived from peripheral blood mononuclear cells (PBMC) through in vitro culture in the presence of high dose interleukin-2 (IL-2). This way is superior to the other way of producing human NK cells as well as CD4$^+$ and CD 8$^+$ T cells, i.e. by allogeneic stimulation of mixed peripheral blood lymphocyte (PBL) populations.

Tumor-specific CTL can be generated by different approaches using either fresh tumor material or known, recombinant tumor antigens, respectively, depending on tumor entity and availability of tissue material. Further details on the generation of tumor-specific CTL are set forth in the Examples.

The therapeutic compositions of the present invention may be administered as a combination of activated non-MHC-restricted T-cells and/or Natural Killer (NK) cells in combination with MHC-restricted T-cells or, alternatively, in combination with therapeutic agents, which induce immune responses of MHC-restricted T cells.

According to one aspect of the present invention, the therapeutic agent for inducing immune responses of MHC-restricted T-cells is a vaccine comprising tumor cells or dendritic cells.

Another aspect is the use of gene therapies, by which an immune response of MHC-restricted T-cells is induced using genetically-engineered tumor cells containing additional genes encoding cytokines or surface molecules that function to improve their capacity to induce specific immune responses. Such genetic modifications can be introduced into tumor cells ex vivo which are then reapplied as vaccines in patients or the genes can be introduced into tumors in vivo by various means. Said transfer of genetic material into tumor cells can be carried out by the following means: In ex vivo approaches, the gene gun technique, electroporation or viral vectors like adenovirus, AAV, retrovirus, EBV, CMV, Herpes simplex and pox viruses, such as MVA among others and cationic lipids for which a number of commercial products is available, can be used. For in vivo approaches, also the gene gun technique can be used as well as viral vectors as adenovirus, AAV, retrovirus, EBV, CMV, Herpes simplex and pox viruses, such as MVA among others cationic lipids, many of them are commercially available, see above.

The following surface molecules can preferably be transferred into tumor cells to improve their immunogenicity: B7.1/B7.2, ICOS ligand and B7-H3. Reference is made to Carreno, B. M. and Collins, M. 2002, The B7 family of ligands and its receptors: new pathways for costimulation and inhibition of immune responses, Ann. Rev. Immunol. 20:29-53. Furthermore, CD40 and CD154 (CD40 ligand) can be used. For further information see: Grewal, I. S, and R. A. Flavell, 1998, CD40 and CD154 in cell-mediated immunity. Ann. Rev. Immunol. 16: 111-135. A further example is the 4-1BB ligand. Reference: Wen T, Bukczynski, J. and Watts, T H. 2002, 4-1BB ligand-mediated costimulation of human T cells induces CD4 and CD8 T cell expansion, cytokine production and the development of cytolytic effector function, J. Immunol. 168: 4897-4906 (2002). Also MHC class II molecules can be used in this context. Reference: Fabre-J W., 2001, The allogeneic response and tumor immunity, Nature Medicine 6:649-652.

The above mentioned therapeutic compositions can be used in the treatment of tumors, which tumors show a low, missing or aberrant expression of MHC class Ia or Ib molecules. According to one preferred embodiment, these tumors show a low, missing or aberrant expression of HLA-C and/or HLA-E molecules.

Examples of these tumors are carcinomas of colon, breast, prostate as well as renal cell carcinoma (RCC) and melanoma.

The non-MHC-restricted cells to be applied either separately or in combination with adoptive transfer of MHC-restricted CTL or applied in parallel with the application of other therapeutic strategies designed to induce MHC-restricted T cell responses in vivo.

The compositions of the present invention, that may, for example, contain LAK cells consisting of mixtures of activated NK and LAK-T cells or cultures containing predominantly LAK-T cells, can be used for adoptive therapy of patients whose tumors show the following characteristics:
1) missing expression of any or all MHC class Ia or class Ib molecules.
2) low expression of MHC class Ia (encoded by HLA-A, B or C loci) or class Ib molecules (encoded by HLA-E or HLA-G locus). This can include tumors showing low expression at any single locus or for any single allele of these four loci.
3) tumors in which the natural levels of HLA-C or HLA-E expression may make them particularly susceptible to NK or LAK-T cells.

The missing expression or low levels of MHC class Ia or class Ib expression can be characteristic of only some tumors cells in the tumor cell population (either primary tumors or metastases) or can be characteristic for all cells in the tumor population (either primary tumors or metastases).

There are different approaches, how the MHC class I expression in tumors can be determined:
a) by immunohistochemical staining of cryopreserved tumor material with cryostat sections using suitable monoclonal antibodies to detect MHC expression (for example (21; 22)
b) by flow cytometry analysis of isolated tumor cells using monoclonal antibodies directed against MHC class I molecules such as the reagent W6/32 (American Type Tissue Culture Collection, Rockville Md., USA) or other antibodies detecting proteins encoded by specific MHC loci or alleles (for example, (23)
c) by molecular analysis of MHC allele expression using oligonucleotide primers that can detect the presence or absence of the various loci in DNA isolated from the tumor cells (i.e. these methods can detect chromosomal alterations in the MHC genes) (for example, (24))
d) by RT-PCR methods to detect lack or diminished levels of RNA encoding MHC class Ia or class Ib alleles (for example, (25))
e) by biochemical analyses using the methods of isoelectric focussing to detect loss of proteins bands corresponding to various MHC class I loci or alleles (for example, (26)) and
f) by functional studies using well-characterized NK or LAK-T cells that are negatively regulated by specific class Ia or class Ib molecules. The failure of tumor cells to inhibit the cytotoxicity of such effector cell populations shows that they would be susceptible to attack by LAK or LAK-T cells having similar specificities.

As controls for each of these methods one can use, when available, corresponding normal tissue. For example in the case of renal cell carcinomas one can use normal kidney parenchyma tissue which is obtained at the time of tumor nephrectomy. Alternatively one can use PBMC as a control.

As a summary, the combination of non-MHC-restricted and MHC-restricted cells can be applied in the following situations:

1) When the tumor cells (either primary tumors or metastases) of the patients show any of the characteristics described above with respect to MHC class Ia or class Ib expression.
2) When patients have undergone immunotherapy treatments in which the therapeutic principle is based on MHC-restricted tumor cell recognition whereby their tumors (either primary or metastases) failed to respond, showed only partial responses or showed a response but subsequently showed renewed growth. These situations indicate that MHC-restricted T cell responses were alone not capable of eliminating all tumor cells.
3) In patients with large tumor burdens (either primary or metastatic lesions) for tumor types that have been shown previously to show aberrant MHC expression in a large percentages of cases, such as melanomas, colon carcinomas, breast cancers and prostate carcinomas (for example (21; 22)).
4) In patients who are to receive immunotherapies based on induction of MHC-restricted T cells, as a parallel treatment to counter-attack the selection for tumor variants that can not be recognized by MHC-restricted effector cells.

Non-MHC restricted cells can be applied in patients subsequent to their receipt of immune therapies based on MHC-restricted responses, simultaneously with such therapies or prior to the application of therapies based on MHC-restricted responses.

The exact mode of application must be coordinated with the other components of the therapy (for example the adoptive transfer of MHC-restricted CTL or the application of various vaccine forms to induce MHC restricted responses). This can be performed according to published studies (for example 11-15).

DETAILED DESCRIPTION

In the following, there is a detailed description of the present invention provided. The basic principles underlying the present invention are illustrated by a special kind of non-MHC restricted cells, i.e. by LAK cells. However, it is noted that the scope of the present invention is not limited to LAK cells and their use.

Figure 1:
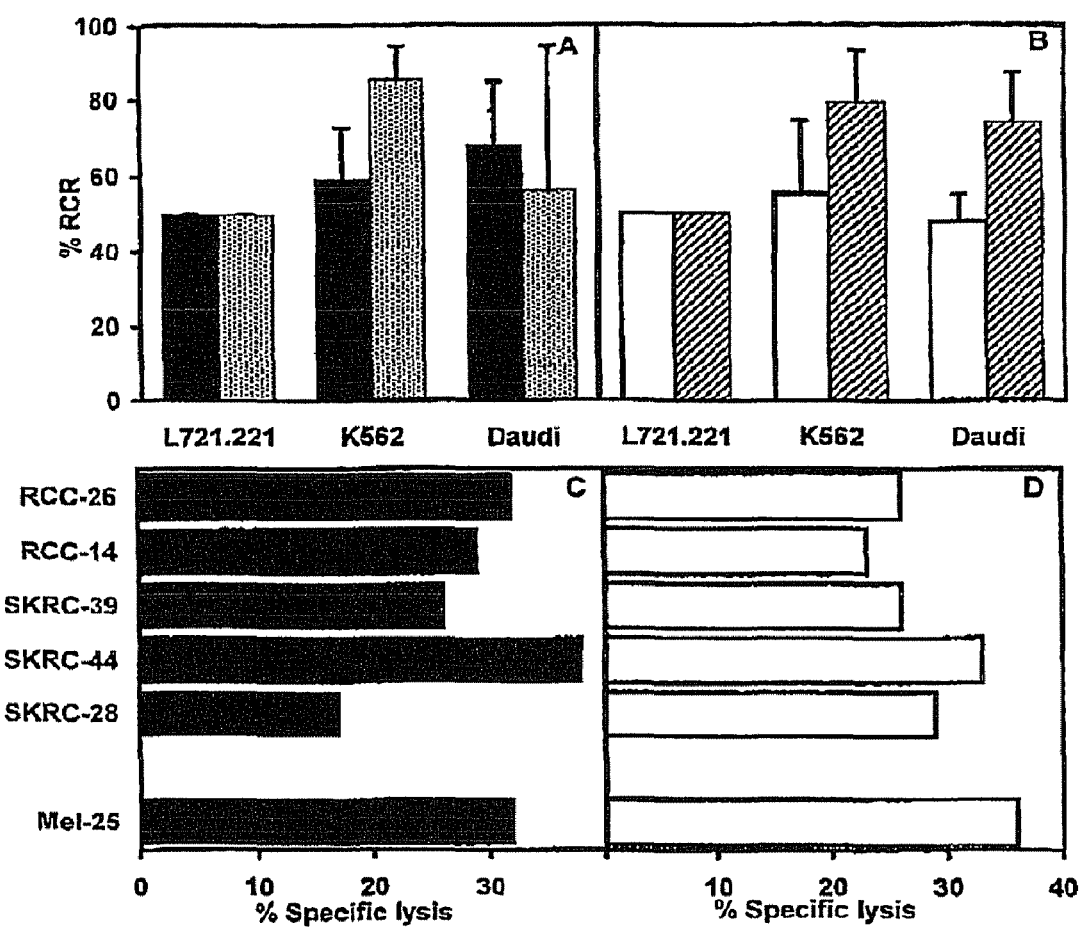
FIG. 1. Cytotoxic activities of LAK cells derived from RCC patients and healthy donors against MHC class I negative and malignant target cells. (A) LAK cells generated from PBMC of two RCC patients, LAK-26 (black bars) and LAK-53 (dotted bars), and (B) two healthy donors, CP-176 (white bars) and CP-41 (hatched bars) were analyzed with three MHC class I negative target cells, L721.221, K562 and Daudi. Results represent mean values±standard deviations of % relative cytotoxic responses (% RCR)(27), calibrated to 50% lysis of L721.221 cells using data derived from five to seven independent experiments. Levels of % specific lysis ranged from 25 to 50%. LAK-26 and LAK-53 cells were tested at an E:T of 10:1; LAK-CP176 and LAK-CP41 at an E:T of 20:1. (C) Specific cytotoxic activity of LAK-26 cells against various RCC lines (RCC and SKRC) and one melanoma line (MEL-25) at an E:T of 20:1. (D) Specific lysis pattern of LAK-CP176 cells against the same RCC and MEL lines at an E:T of 20:1.

LAK Cells from RCC Patients and Healthy Donors Recognize MHC Class I Negative Target Cells and HLA Class I Positive Tumor Lines LAK cells generated from PBMC of patients with RCC and healthy donors were tested for cytotoxic activity directed against MHC class I negative target cells and various tumor cell lines. FIG. 1 summarizes composite results of several independent experiments in which the HLA class I negative target cells L721.221, K562 and Daudi were efficiently lysed by four different LAK populations. No substantial differences in levels of cytotoxic activity were observed between LAK-26 and LAK-53, derived from two RCC patients (FIG. 1A) and LAK-CP176 and LAK-CP41, derived from two healthy control donors (FIG. 1B). The patient-derived LAK-26 were able to lyse the autologous RCC line (RCC-26) and, in addition, they could recognize various allogeneic RCC lines (SKRC) as well as the MEL-25 melanoma line, independent of HLA background (FIG. 1C). The control donor-derived LAK-CP176 line lysed these various tumor cell lines in a similar fashion (FIG. 1D). All of these tumor lines were shown to be class I positive through binding of the class I-specific mab, W6/32 (data not shown). These results demonstrated that the LAK populations were able to recognize target cells in a non-MHC-restricted manner and lysis was not specific for any single tumor entity.

LAK Populations are Composed Primarily of $CD4^+$ and $CD8^+$ T Cells

Phenotype analyses of lymphocyte subsets were made of the expanded LAK cultures derived from the four different donors utilized in these studies. Table 1 shows the distribution of $CD3^-CD56^+$ NK cells and $CD3^+CD56^-$ T cells in these LAK populations. Differences between LAK cells derived from RCC patients and healthy donors were not evident: $CD3^+$ T cells were the major cell type, representing more than 95% of the cells in all samples. While the LAK-CP176 culture was dominated by $CD8^+$ T cells, the other LAK samples contained approximately equal numbers of $CD4^+$ and $CD8^+$ T cells. In contrast, $CD3^-CD56^+$ NK cells were present in only very low numbers, ranging from 0-6% of total cells. These results revealed that the culture conditions used for generation and maintenance of these LAK cells led primarily to expansion of the T cell fraction of lymphocytes rather than the adherent fraction of NK cells. The phenotype of these LAK cell lines indicated that the major cytolytic component was attributable to activated T cells. In fact, depletion of the small remaining fraction of NK cells from the mixed LAK populations did not alter their cytotoxic potential or specificity (data not shown).

Figure 2:
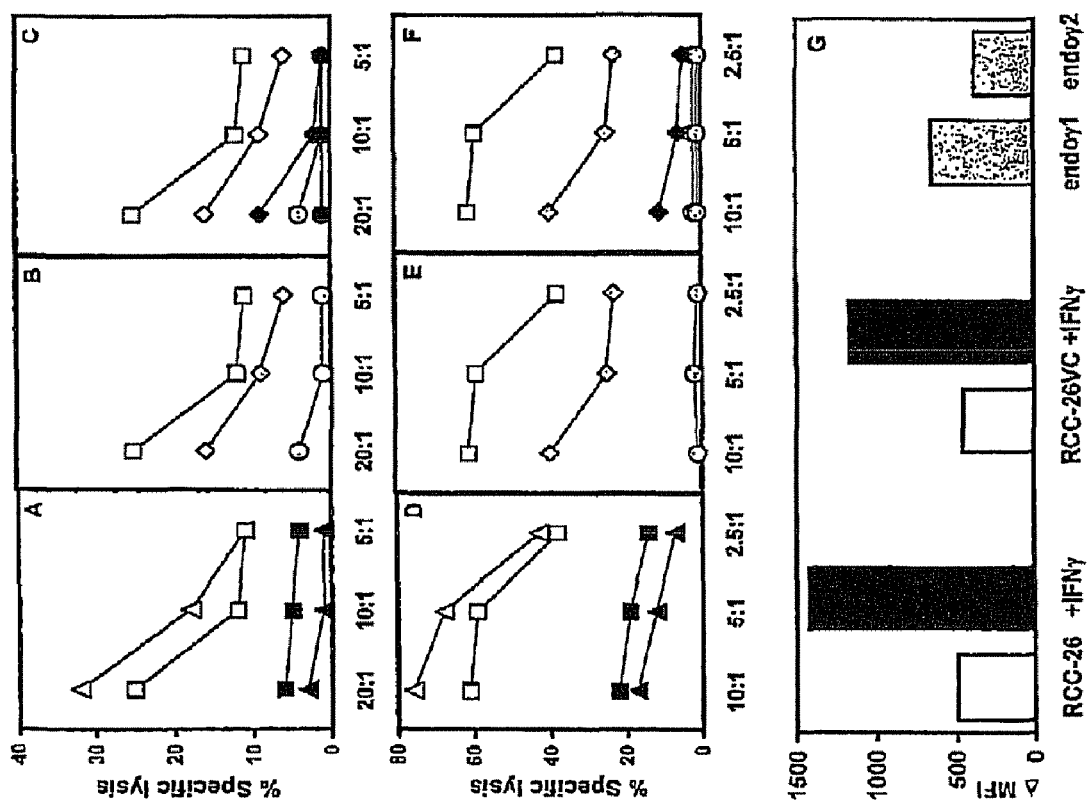
FIG. 2. Inhibition of lysis by endogenous or exogenous IFNγ modulation of RCC-26 cells. Specific cytotoxic activity of LAK-26 T cells (A-C) and B.3NK cells (D-F) against RCC-26 cells (Δ), vector control cells RCC-26VC (□) without IFNγ (open symbols) or after 96 h stimulation with 1000 U/ml IFNγ (black symbols). Unmodified RCC-26 and RCC-26VC cells were directly compared for their sensitivity to lysis by LAK-26 (A) and B.3NK (D). Two endogenous IFNγ expressing RCC-26 lines, endoγ1 (grey ○) and endoγ2 (grey ◇) were used as target cells in comparison to RCC-26VC control cells (□) for LAK-26 cells (B) and B.3NK cells (E), respectively. Cytotoxic activity of LAK-26 (C) and B.3NK cells (F) against endoγ1 and endoγ2 cells without (○; ◇) or after 96 h stimulation with exogenous IFNγ (●; ◆). All effector/target combinations were tested simultaneously. Data are shown as % specific lysis for one of four independent experiments. (G) Expression of MHC class I on RCC-26 tumor cells and transduced variants using the pan class I-specific mab W6/32. The data represent corrected mean fluorescence intensities (ΔMFI) evaluated by subtracting MFI with isotype control mab from MFI with specific mab for one of nine representative experiments.

MHC Class I Enhancement is Associated with IFNγ-Mediated Inhibition of LAK-T Cells and Activated NK Cells It has been shown previously that IFNγ treatment of tumor cells can lead to resistance to purified NK cells and to LAK cells (29; 30)). To determine whether MHC expression could also affect tumor cell sensitivity to LAK-T cells, RCC-26 cells were analyzed after enhancement of their class I expression through exogenous IFNγ stimulation. Alternatively, the RCC-26 line was transduced with human IFNγ cDNA, leading to endogenous cytokine production and subsequent upregulation of class I expression (31). Susceptibility of these different IFNγ-modulated RCC-26 cells to lysis was assessed using autologous LAK-26 T cells (FIG. 2A-C). Purified B.3NK cells which were shown previously to exclusively express p58.2 receptors of the KIR family that bind HLA-C molecules of the Cw1, 3, 7 subgroup were included for comparison (FIG. 2D-F). Unmodified RCC-26 cells and the control line carrying empty vector (RCC-26VC) were lysed by both effector cell types, whereby the activated NK cells showed a stronger lytic capacity. Following stimulation with exogenous IFNγ both tumor lines displayed substantial resistance to lysis by both LAK-T and NK cells (FIG. 2A, D). A similar degree of resistance was observed with one IFNγ transductant (endoγ1) whereas the second transductant (endoγ2) showed only partial resistance to both effector populations (FIG. 2B, E). However, further stimulation with IFNγ led to an increased resistance of this transductant to both LAK-26 T cells and B.3NK cells (FIG. 2C, F). This resistance was comparable to that induced by exogenous IFNγ stimulation of RCC-26 and RCC-26VC cells. In parallel studies, the LAK-53, LAK-CP41 and LAK-CP176 T cells showed cytotoxic patterns like those of LAK-26 T cells and B.3NK cells, demonstrating a general correlation between IFNγ-induced effects and resistance to LAK-derived cytotoxic T cells (data not shown).

The decrease in LAK-T and control NK activity following interaction with the various target cells was consistently seen in all experiments in which increases in class I expression were detected by flow cytometry. FIG. 2G shows representative results of one of numerous experiments analyzing the enhancement of MHC class I expression by IFNγ in RCC-26 cells. Even though RCC-26 and RCC-26VC cells constitutively expressed substantial levels of class I molecules, expression was increased following IFNγ stimulation, as detected by staining with the class I-specific mab, W6/32. While the total levels of MHC expression varied among the different cell lines, these were reproducible and apparently reflected variations in the responsiveness of the individual lines to IFNγ induction. Interestingly, the endoγ2 line displayed, lower constitutive levels of MHC molecules when compared to endoγ1 cells. This transductant was also more susceptible to LAK-T- and NK-mediated cytotoxicity. However, stimulation of endoγ2 cells with exogenous IFNγ led to enhanced class I expression (data not shown) and increased resistance to both effector cell types (see FIG. 2C, F). In additional experiments it was shown that other tumor cell lines acquired resistance to LAK-T cells following their treatment with IFNγ (data not shown).

The availability of a cell line derived from normal kidney parenchyma of patient 26 (NKC-26) (32) allowed assessment of whether the IFNγ-induced inhibition of LAK-T and NK cytotoxicity was restricted to tumor cells or also affected lysis of normal epithelial cells. NKC-26 cells were lysed by autologous LAK-26 T cells (FIG. 3A) and allogeneic B.3NK cells (FIG. 3B), demonstrating that these effector cells were not tumor specific. As seen with RCC-26 cells, exogenous IFNγ stimulation of NKC-26 cells resulted in substantial inhibition of cytotoxicity by both LAK-T cells and activated NK cells, revealing that IFNγ-induced resistance was also not tumor specific. In studies not shown it was found that allogeneic LAK-T cells could lyse the NKC-26 line and that IFNγ stimulation led to its partial resistance, indicating that this effect was not limited to autologous LAK-T cells.

Figure 3:
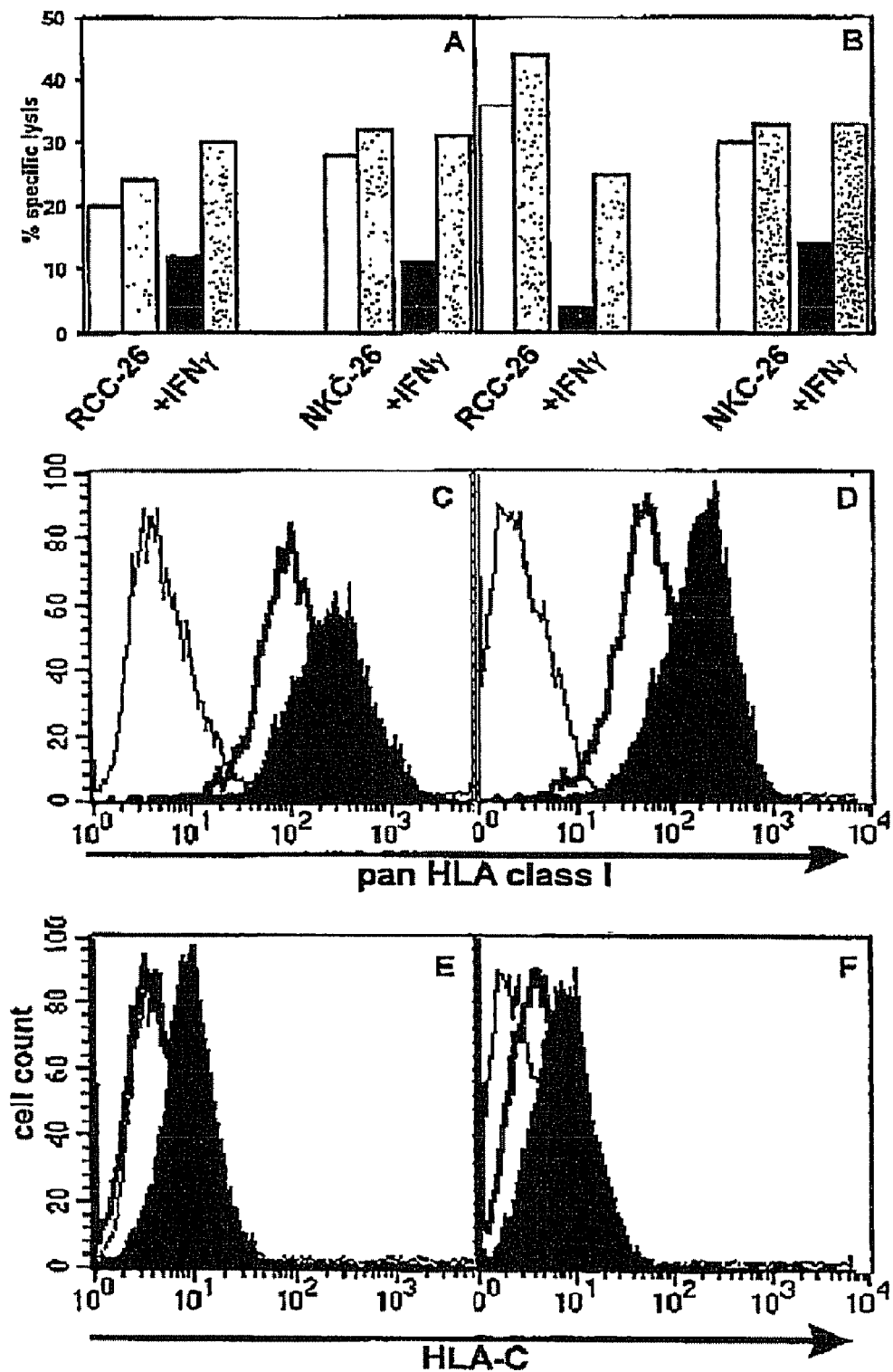
FIG. 3. LAK and B.3NK activities are not tumor specific and inhibition can be reversed by blocking with HLA class I mab. (A) LAK-26 and (B) B.3NK cells were tested in parallel against tumor (RCC-26) cells and normal kidney cells (NKC-26) in the presence of control mab (MOPC21) without IFNγ (white bars) or following 96 h IFNγ stimulation (black bars). Cells preincubated with class I-specific mab (W6/32) for 30 min are indicated by hatched bars in both graphs. RCC-26 (C+E) and NKC-26 (D+F) were analyzed for HLA class I surface expression using W6/32 for general class I staining (C+D) and the HLA-C-specific mab, L31 (E+F). Unstimulated RCC-26 or NKC-26 cells are shown in bold open graphs, IFNγ-stimulated cells are displayed as filled graphs and control staining with mab MOPC21 is shown with open thin graphs.

Parallel studies analyzing class I expression following IFNγ stimulation showed increased binding of W6/32 antibody by both RCC-26 (FIG. 3C) and NKC-26 cells (FIG. 3D). Likewise, the levels of HLA-C molecules which serve as the ligands for the p58.2 inhibitory receptors that govern the activity of B.3NK cells were found to be increased on both cell lines using mab L31 (FIG. 3E, F). The weak staining pattern observed with mab L31 may be explained by its preferential reactivity with $β_2$m-free heavy chains of HLA-C molecules (33).

MHC Class I-Specific Antibody Reverses Inhibition of LAK-T Cell Cytotoxicity

Since IFNγ regulates expression of many different genes, functional inhibition studies using mab to block class I ligands on target cells were used to demonstrate that these molecules directly contributed to the downmodulation of LAK-T and NK activity. Preincubation of IFNγ-stimulated RCC-26 or NKC-26 cells with W6/32 mab led to reversal of inhibition of both effector populations (FIG. 3A, B). Thus, resistance of normal epithelial cells and tumor cells was mediated by class I molecules and antibody masking of class I surface expression could restore susceptibility of both target cells to lysis.

The class I-dependent inhibition of LAK-T cytotoxcity was confirmed by extended blocking studies summarized in Table 2. Cytotoxic activities of LAK-T cells (LAK-26, LAK-CP41) and B.3NK cells against various target cells were analyzed in the presence of W6/32 or isotype control mab. Preincubation of unstimulated RCC-26 and RCC-26VC cells with W6/32 mab led to small increases in lysis by the different effector cells when compared to isotype controls. Addition of W6/32 mab led to substantial reversal of the inhibition of lysis seen with the IFNγ-stimulated RCC-26 and RCC-26VC cells. Moreover, lysis of both IFNγ-expressing transductants was substantially increased in the presence of W6/32 mab The consistently improved cytotoxicity achieved through masking of class I molecules was also observed with a second RCC line and a corresponding IFNγ transductant (data not shown). These results demonstrated that class I molecules contributed directly to the IFNγ-mediated inhibition of LAK-T cells and activated NK cells.

HLA Class Ia and Class Ib Molecules can Inhibit LAK-T Cytotoxicity

Figure 4:
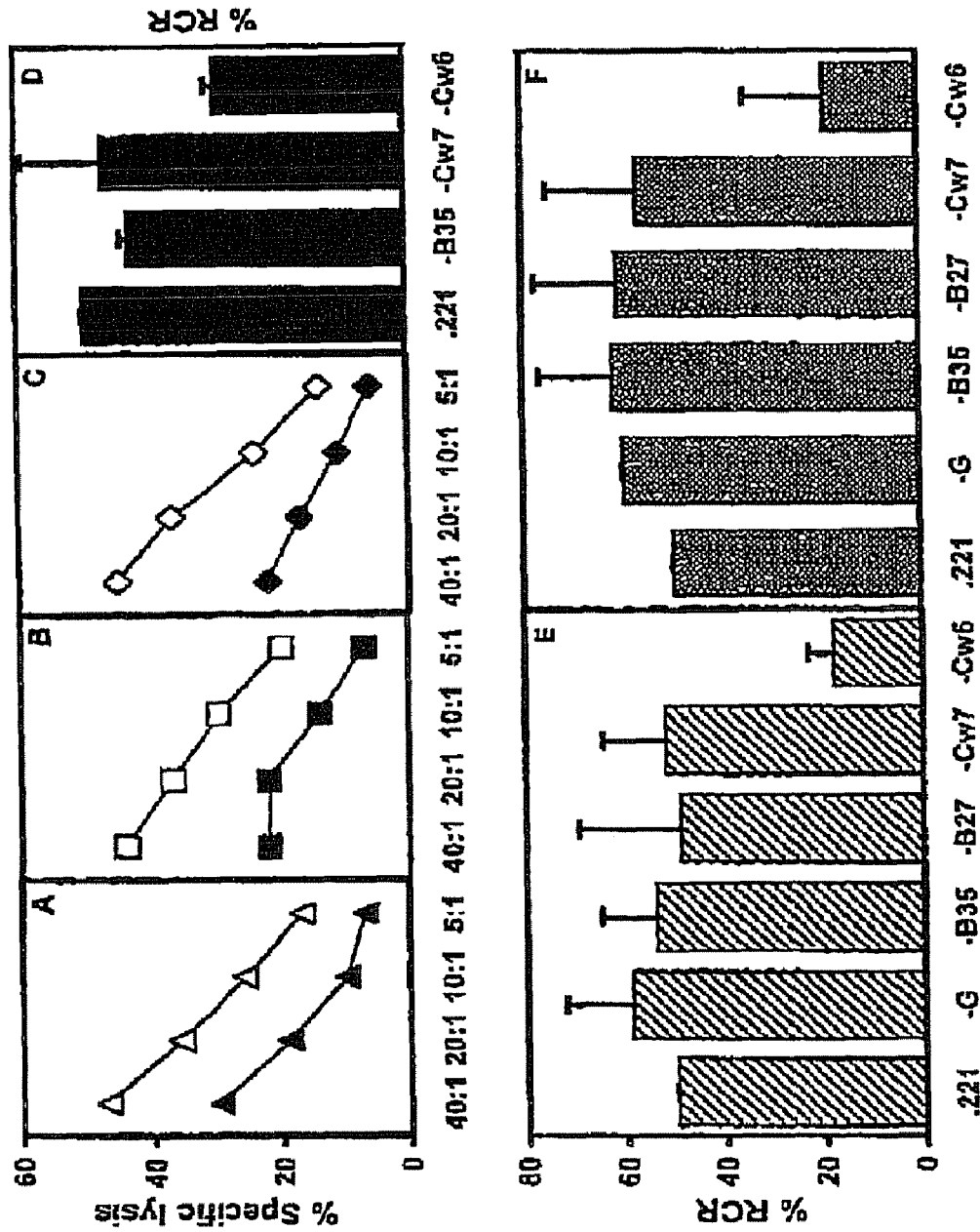
FIG. 4. Inhibition of LAK cytotoxicity by HLA class Ia and Ib molecules transfected into class I negative cells. (A-D) Cytotoxicity of LAK-26 cells was tested using different class I negative target cells following modification to express class I molecules. (A) The class I negative L721.221 (Δ) line compared to the class I positive HLA-hemizygous variant L721.112 line expressing the HLA-A1, Cw7, B8 haplotype (▲). (B) Class I negative Daudi cells (□) in comparison with class I positive Daudi-$\beta_2$m transfectant potentially expressing A*0102, A*6601, B*5801, B*5802, Cw*0302, and Cw*0602 (■)(28). (C) Class I negative K562 cells (◇) and the corresponding HLA-E expressing transfectant (◆). (D) L721.221 cells compared with transfectants expressing single HLA alleles (B*3501, Cw*0702, Cw*0602) showing comparable levels of MHC expression (data not shown). Data represent mean values+SD of % RCR of three independent experiments at an E:T of 20:1. (E) LAK-CP41 and (F) LAK-CP176 lysis of L721.221 cells and transfectants expressing HLA-G, B*3501, B*2705, Cw*0702 and Cw*0602 at an E:T of 20:1. Data for A-C represent % specific lysis and D-F values represent mean values+SD of % RCR using 50% lysis of L721.221 as a reference from three or more independent experiments (27). The values of % specific lysis of L721.221 ranged from 35% to 58%.

Since LAK-T cells efficiently lysed class I negative target cells we investigated whether expression of class I molecules in such cells could directly inhibit LAK-T activity. The class I negative cell line L721.221 was derived from a class I positive lymphoblastoid cell line (L721) by irradiation induced mutagenesis with selection for sequential HLA loss variants. The L721.112 line represents a hemizygous cell line generated in this series which still expresses one of the two parental haplotypes (HLA-A1, B8, Cw7). While L721.221 cells were very sensitive to LAK-26 T cell-mediated lysis, the expression of class I molecules by L721.112 cells provided partial protection (FIG. 4A). The Daudi cell line does not produce β$_2$m and thereby does not express stable class I molecules at the cell surface. Transfection of the β$_2$m gene into Daudi cells reconstituted their expression of class I molecules (28) which was confirmed by staining with W6/32 mab (data not shown). The unmodified cell line was efficiently lysed by LAK-26 T cells whereas transfectant cells showed substantial resistance (FIG. 4B). It was also found that the K562 cells became partially resistant to LAK-26 T cell-mediated lysis following transfection with the class Ib gene encoding HLA-E molecules (FIG. 4C). L721.221 cells that were genetically modified to express 835, HLA-Cw6 and HLA-Cw7 molecules were also analyzed as target cells for LAK-26 T cells. While no reproducible inhibition was seen by HLA-B35 or HLA-Cw7 molecules, partial resistance (25%) was induced by HLA-Cw6 expression (FIG. 4D). These results confirmed that class I molecules alone could directly inhibit LAK-26 T cell cytotoxicity.

Insight into the fine specificity of MHC inhibition was also obtained for other LAK-T cells (LAK-CP41 and LAK-CP176) since it was possible to specifically inhibit their lysis of L721.221 cells by more than 50% through expression of HLA-Cw6 (FIG. 4E, F). In contrast, expression of HLA-G, -B35 and -B27 and -Cw7 molecules in these cells did not induce resistance to LAK-T cells. An inhibitory influence of HLA-E molecules appeared unlikely since the signal peptide of HLA-G can bind to HLA-E molecules, allowing their stable surface expression (34). Therefore the L721.221-G cells can simultaneously express both HLA-G and HLA-E molecules. Because these cells did not cause inhibition it appears that HLA-E played no regulatory role in these two LAK-T cell populations.

LAK-Derived CD4 T Cells are Also Negatively Regulated by MHC Molecules

Figure 5:
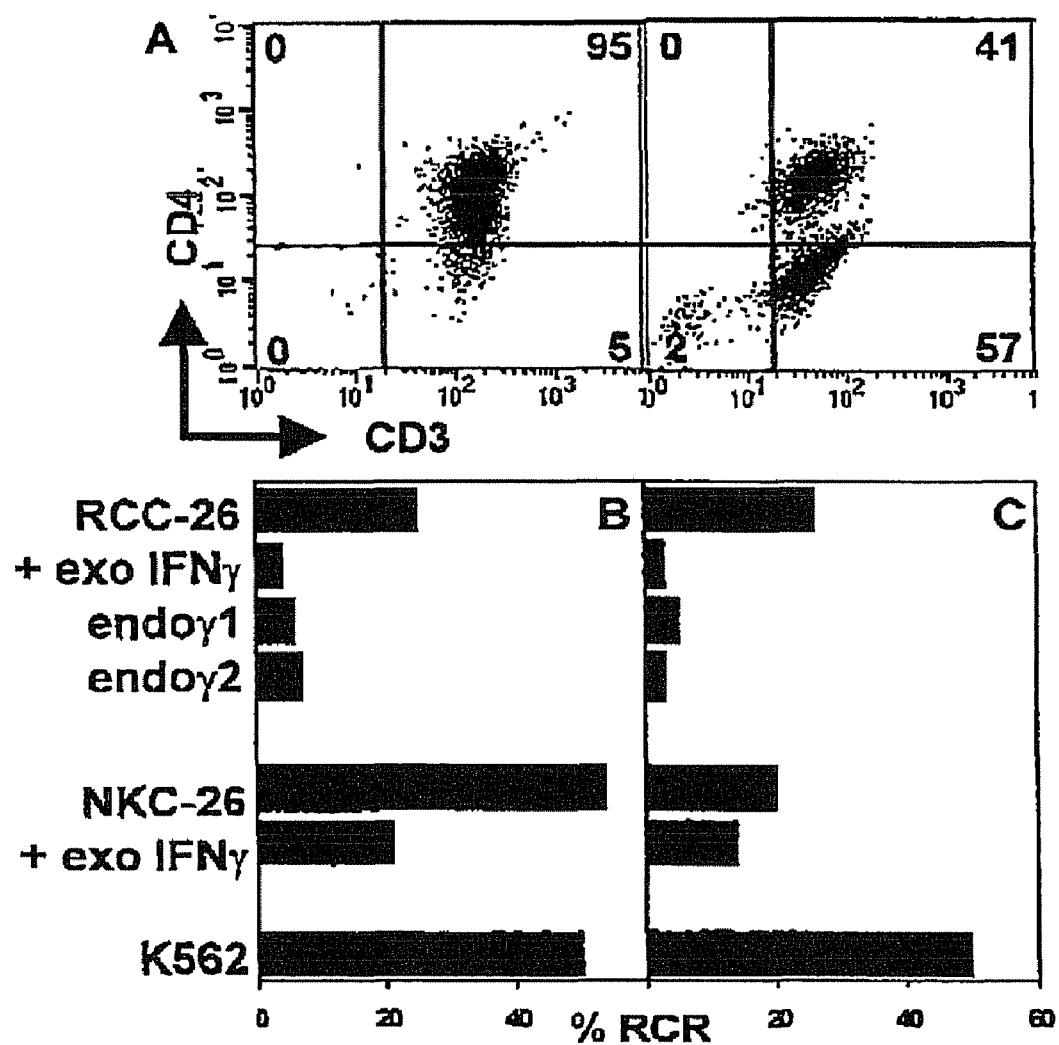
FIG. 5. Negative regulation of cytotoxicity of $CD4^+$ LAK-T cells. (A) Phenotype analysis of enriched $CD4^+$ LAK-26-derived T cells (left) and the mixed LAK-26 population (right). CD3 and CD4 staining is shown. The cytotoxic pattern of enriched $CD4^+$ LAK-26-derived T cells (B) was compared to that of mixed LAK-26 cells (C). Data represent % RCR using 50% lysis of K562 cells as a reference value. The % specific lysis for K562 by $CD4^+$ T cells was 26% and of the mixed population was 30%.

Enrichment of CD4$^+$ lymphocytes was made by depleting the CD8$^+$ cells from a mixed LAK-T cell population. To confirm directly that these T cells were cytolytic and their activity could be downregulated by exposure to IFNγ-modulated tumor cells, the CD4-selected T cells (FIG. 5A left) were compared to the unseparated LAK-26 T cell population containing both CD4 and CD8 cells (FIG. 5A, right). The highly purified CD4$^+$ T cells were able to lyse RCC-26, NKC-26 and K562 target cells in a manner analogous to the unseparated LAK-T population (FIGS. 5B and C). Furthermore, IFNγ-modulation (exogenous stimulation or endogenous expression) of RCC-26 and NKC-26 cells led to inhibition of lysis of the purified CD4$^+$ T cells in a similar fashion to the unseparated population of LAK-T cells.

LAK-T Cells do not Express Known Inhibitory Receptors

The demonstration that the LAK-T cells were regulated by class I-mediated inhibition suggested that they might carry inhibitory receptors like those expressed by NK cells. Therefore, surface phenotyping to identify such receptors was made using mab specific for several known inhibitory receptors that interact with HLA-B, C or E molecules. As summarized in Table 3, inhibitory receptors belonging to the KIR immunoglobulin superfamily (p58.1, p58.2 or NKB1) were not present on the T cells. Small percentages of both CD3$^+$ and CD3$^-$ cells (3-7%) expressed CD94 molecules. In NK cells it has been found that CD94 associates with the NKG2A coreceptor molecule to create an HLA-E-specific heterodimeric inhibitory receptor. Because K562 cells expressing HLA-E substantially inhibited LAK-26 T cell-mediated cytotoxicity (see FIG. 4C), we expected to find T cells bearing such receptors in this population. However, less than 1% of LAK-26 T cells bound NKG2A antibody (data not shown). Likewise, because LAK-26, LAK-CP41 and LAK-CP176 were partially inhibited by HLA-Cw6 molecules (see FIG. 4D-F), some T cells expressing p58.1 receptors were expected, but were also not found in these populations. Thus, the known inhibitory receptors governing NK cell inhibition by HLA-C and HLA-E ligands were not expressed to any appreciable degree by LAK-T cells, even though the specific class I ligands characteristic for these receptors were apparently delivering inhibitory signals to these T cells.

EXAMPLES

The following examples are set forth for illustrative purposes and should not be considered as limiting the scope of protection of the present invention.

Generation of LAK Cells:

Blood samples are obtained using either heparin (50 units/ml) (for example: Heparin-Natrium, Braun Melsungen AG) or defibrination to prevent coagulation. To obtain larger numbers of PBMC an apheresis can be performed to obtain the equivalent of 1-4 liters of blood (methods for blood preparation are described in (35).

Peripheral blood mononuclear cells (PBMC) are isolated by Ficoll/Hypaque (for example: Biocoll Separating Solution, Biochrom AG) density gradient centrifugation using standard methods (35).

PBMC are washed 2× in phosphate buffered saline (PBS) and cultured directly or cryopreserved for future use. For cryopreservation, PMBC are frozen at concentrations of 5-20×10$^6$ cells/ml in 1 ml aliquots in RPMI culture medium containing 25-50% autologous serum and 10% DMSO in RPMI 1640 medium (for example: RPMI 1640 Medium, Fa. Invitrogen) and stored in the gas phase of a liquid nitrogen tank. Cryopreserved PBMC are thawed by adding RPMI medium containing 50% human serum dropwise to a partially thawed cell sample. Following transfer into a plastic centrifuge tube the volume of medium is increased to 3-5 ml and the cells are washed 2× (35).

Freshly isolated PBMC or thawed PBMC are resuspended after the 2nd wash in "LAK" medium at a density of 1×10$^6$ cells/ml.

LAK medium can be prepared in one of two ways:
a) RPMI culture medium containing 15% human serum and 1000 units/ml of recombinant human interleukin 2 (IL-2) (for example Proleukin, Cetus, Emeryville Calif., USA)
b) RPMI culture medium containing 15% human serum and 1000 units/ml IL-2 and 1% (vol/vol) of phytohemagglutinin (for example: Difco Laboratories, Detroit Mich., USA)

PBMC are cultured in 50 ml culture flasks (for example Falcon, Becton-Dickinson, San Jose, Calif., USA) standing upright containing a volume of 4-15 ml at 37° C. and 5% $CO_2$ for 72-96 hours. Thereafter, the cultures are counted and cell densities readjusted to 1×10$^6$ cells/ml using LAK medium without PHA. When the volume of a culture reaches >15 ml it is divided between two flasks and cultures continued under the same conditions.

Larger numbers of cells can be obtained by scaling up the volume of the cultures into 250 ml culture flasks (Falcon, Becton-Dickinson, San Jose, Calif., USA) (>45-150 ml/flask). If enough PBMC are available (for example derived from an apheresis) several 250 ml flasks can be cultured simultaneously up to high cell numbers such as 10$^9$ cells.

At the completion of the culture period the activated cells can be phenotyped for lymphocyte subpopulations to determine the composition of NK and LAK-T cells. It is our experience that after two to three weeks of culture the populations are predominantly LAK-T cells. Functional assessment of their cytolytic potential can be made using a standard chromium release assay using Daudi and K562 cell lines as target cells (27).

Activated LAK cells can be cryopreserved for future use using the same freezing protocol as described above or applied directly after completion of the culture phase.

Generation of Tumor-Specific Cytotoxic T Cells (CTL)

Tumorspecific CTL can be generated by different approaches using either fresh tumor material or known, recombinant tumor antigens, respectively, depending on tumor entity and availability of tissue material.

In the rare cases where an in vitro tumor line is available, CTL can be generated by stimulation of PBL against irradiated tumor cells. Briefly, tumor cells were grown in 24-well plates and, following irradiation of the tumor cells, autologous PBL were added in human serum containing medium, optionally supplemented with IL-2 and/or IL-4. Every 7 to 10 days, T cells were harvested and again restimulated with irradiated tumor cell cultures. After several rounds of restimulation, the activity and specificity of the mixed CTL populations were tested using standard chromium release, ELISPOT, or cytokine secretion assays.

Alternatively, if no tumor line is available, a lysate of tumor tissue can be used in vitro to pulse dendritic cells (DC) in order to promote the presentation of specific peptides derived from tumor antigens by these professional antigen presenting cells (APC). With respect to known tumor antigens, in the case of the malignant melanoma, for instance, synthetic peptides or recombinant protein fragments derived from known melanoma antigens are used to pulse DC. Another principle of tumor antigen presentation by DC is based on the generation of tumor-derived RNA which can be used to directly pulse DC by endogenous expression of tumor-RNA. The procedures for restimulation and for the analysis of activation and specificity of mixed CTL populations are described above, i.e. standard chromium release, ELISPOT, or cytokine secretion assays.

Independent of the procedure for CTL generation, most approaches must deal with similar limitations such as very low frequency of tumor-specific CTL precursors in the blood, time consuming and laborous production of tumor-specific CTL and the availability of individual tumor material or common tumor antigens.

Effector Cells and Target Cells

PBMC obtained from RCC patients undergoing tumor nephrectomy or from healthy donors were used for the generation of LAK cells by culture in RPMI 1640 medium supplemented with 2 mM L-glutamine, 1 mM pyruvate, 100 U/ml penicillin/streptomycin (complete medium), 15% heat-inactivated, pooled human serum, 1% phytohemagglutinin (PHA, Difco-Laboratories, Detroit, MC) and 1000 U/ml rIL-2 (Proleukin, Cetus Corp. Emeryville, Calif.). These cultures were maintained over several weeks in order to obtain expanded populations of activated CD4$^+$ and CD8$^+$ T cells. LAK-derived CD4$^+$ T cells were enriched by magnetic bead separation (Dynal, Oslo, Norway) by depleting CD8$^+$ T and NK cells according to the manufacturer's instructions. Human NK cells were activated as described previously and purified NK cells were obtained by depleting T cells using CD4- and CD3-coated immunomagnetic beads (Dynal). The enriched NK cell line used in these studies, designated as B.3NK cells, was maintained in complete medium supplemented with rIL-2 (300 U/ml).

Cytotoxicity of these effector cells was assessed using Epstein-Barr virus transformed lymphoblastoid cell lines (LCL) derived from the L721 cell line. The L721.112 cell line represents a hemizygous variant of L721 that expresses the A1, Cw7, B8 haplotype (kindly provided by T. Spies, Fred Hutchinson Cancer Research Center, Seattle). The L721.221 cell line does not express any MHC class I molecules (36). This line was transfected to express the class I alleles, B*3501, B*3702, Cw*0602, and Cw*0702, as described. An HLA-E transfectant of K562 was generated by transfecting hybrid DNA cloned into the pcDNA3 vector encoding exon 1 of HLA-A2 and exons 2-7 of HLA-E. This construct allows HLA-E surface expression by stabilization of the HLA-E heavy chain with an HLA-A2-derived peptide. Daudi cells transfected with the gene encoding beta-2-microglobulin ($\beta_2$m) (28) were kindly provided by P. Parham (Stanford University, Palo Alto, Calif.).

The RCC-26 tumor line was established from a primary stage I (T1,G2,N0, M0) tumor of patient 26 (HLA alleles: A*0201, A*3303, B*4101, B*5101, Cw*1502, Cw*1701) and the normal kidney line, NKC-26, was established from normal kidney parenchyma obtained at the time of tumor nephrectomy (32). Both cell lines were cultured in 10% FCS containing complete medium without antibiotics. RCC-26 cells were transduced with the human IFNγ cDNA, using the retroviral system described previously (37). Two IFNγ-expressing lines (designated as endoγ1 and endoγ2) were generated by independent retroviral transduction (31). A control line (RCC-26VC) was made using the same vector without IFNγ cDNA (31). Exogenous IFNγ stimulation of tumor cells was performed for 96 h in medium containing 1000 U/ml of recombinant IFNγ (Roche, Basel, Switzerland).

Cell-Mediated Cytotoxicity Assay

Cell-mediated lysis was quantitated in standard 4 h chromium-51 release assays (27). Spontaneous release was determined by incubating target cells alone, total release by directly counting labeled cells. Percent cytotoxicity was calculated as follows: % specific lysis=(experimental cpm−spontaneous cpm/total cpm−spontaneous cpm)×100. Duplicate measurements of three step titrations of effector cells were used for all experiments. To compare data from independent experiments, % relative cytotoxic responses (% RCR) were calculated using specific lysis of untransfected L721.221 or K562 cells in each experiment as reference values of 50%. The % lysis of other target cells was determined in relation to the reference value and expressed as % RCR (27).

To evaluate the influence of MHC class I molecules, the class I-specific mab, W6/32 was added to target cells 30 min prior to addition of effector cells: mab W6/32 was used as ascites diluted 1:100 and UPC10 (IgG2a) (Sigma, Deisenhofen, Germany) was used as the isotype control.

Immunophenotyping of Effector Cells and Target Cells

Effector cells were characterized using a panel of lymphocyte specific mab: FITC- or PE-labeled mab specific for CD3 (UCHT1), CD4 (13B8.2), CD8 (B9.11), CD56 (NKH-1), were purchased from Beckmann/Coulter, Westbrook, Me. Inhibitory receptor expression was analyzed with FITC- or PE-labeled mab specific for p58.1 (KIR2DL1, EB6), p58.2 (KIR2DL3, GL183), CD94 (HP-3B1) all purchased from Beckmann/Coulter and NKB1 (KIR3DL1, DX9) from Pharmingen, San Diego, Calif. Cells were incubated for 30 min on ice, washed twice, fixed with PBS-1% paraformaldehyde and analyzed using flow cytometry (FACS-Calibur, Becton/Dickinson, San Jose, Calif.).

Tumor cells were tested for surface expression of MHC molecules by flow cytometry using culture supernatants of the W6/32 hybridoma (American Type Culture Collection, Rockville, Md.). The HLA-C-specific mab L31 was kindly provided by P. Giacomini, Milano, Italy (33). Mab UPC10 and MOPC21(Sigma) were used as negative controls. Cells were incubated with mab for 90 min on ice, washed twice with PBS and incubated with PE-conjugated goat-anti-mouse immunoglobulin (F(ab)$_2$, 115-116-146; Dianova, Hamburg, Germany) for 30 min and analyzed using flow cytometry.

REFERENCE LIST (1) Long E O. Regulation of immune responses through inhibitory receptors. Annu Rev Immunol 1999; 17:875-904.
(2) Colonna M, Moretta A, Vely F, Vivier E. A high-resolution view of NK-cell receptors: structure and function. Immunol Today 2000; 21(9):428-431.
(3) Ravetch J V, Lanier L L. Immune inhibitory receptors. Science 2000; 290(5489):84-89.
(4) Lopez-Botet M, Bellon T, Llano M, Navarro F, Garcia P, de Miguel M. Paired inhibitory and triggering NK cell receptors for HLA class I molecules. Hum Immunol 2000; 61(1):7-17.
(5) Braud V M, Allan D S, O'Callaghan C A, Soderstrom K, D'Andrea A, Ogg G S et al. HLA-E binds to natural killer cell receptors CD94/NKG2A, B and C [see comments]. Nature 1998; 391(6669):795-799.
(6) Bukowski R M. Natural history and therapy of metastatic renal cell carcinoma: the role of interleukin-2. Cancer 1997; 80(7):1198-1220.
(7) Jayson G C, Middleton M, Lee S M, Ashcroft L, Thatcher N. A randomized phase II trial of interleukin 2 and interleukin 2-interferon alpha in advanced renal cancer. Br J Cancer 1998; 78(3):366-369.
(8) Jonasch E, Haluska F G. Interferon in Oncological Practice: Review of Interferon Biology, Clinical Applications, and Toxicities. Oncologist 2001; 6(1):34-55.
(9) Negrier S, Escudier B, Lasset C, Douillard J Y, Savary J, Chevreau C et al. Recombinant human interleukin-2, recombinant human interferon alfa-2 a, or both in metastatic renal-cell carcinoma. Groupe Francais d'Immunotherapie. N Engl J Med 1998; 338(18):1272-1278.
(10) Rosenberg S A, Lotze M T, Muul L M, Leitman S, Chang A E, Ettinghausen S E et al. Observations on the systemic administration of autologous lymphokine-activated killer cells and recombinant interleukin-2 to patients with metastatic cancer. N Engl J Med 1985; 313(23):1485-1492.
(11) Rosenberg S A. Adoptive immunotherapy of cancer using lymphokine activated killer cells and recombinant interleukin-2. Important Adv Oncol 1986; 55-91.
(12) Rosenberg S. Lymphokine-activated killer cells: a new approach to immunotherapy of cancer. J Natl Cancer Inst 1985; 75(4):595-603.
(13) Hoffman D M, Gitlitz B J, Belldegrun A, Figlin R A. Adoptive cellular therapy. Semin Oncol 2000; 27(2):221-233.
(14) Rosenberg S A. Interleukin-2 and the development of immunotherapy for the treatment of patients with cancer. Cancer J Sci Am 2000; 6 Suppl 1:S2-S7.
(15) Kruit W H, Schmitz P I, Stoter G. The role of possible risk factors for acute and late renal dysfunction after high-dose interleukin-2, interferon alpha and lymphokine-activated killer cells. Cancer Immunol Immunother 1999; 48(6):331-335.
(16) Tomita Y, Katagiri A, Saito K, Imai T, Saito T, Tanikawa T et al. Adoptive immunotherapy of patients with metastatic renal cell cancer using lymphokine-activated killer cells, interleukin-2 and cyclophosphamide: long-term results. Int J Urol 1998; 5(1):16-21.
(17) Kruit W H, Goey S H, Lamers C H, Gratama J W, Visser B, Schmitz P I et al. High-dose regimen of interleukin-2 and interferon-alpha in combination with lymphokine-activated killer cells in patients with metastatic renal cell cancer. J Immunother 1997; 20(4):312-320.
(18) Law T M, Motzer R J, Mazumdar M, Sell K W, Walther P J, O'Connell M et al. Phase III randomized trial of interleukin-2 with or without lymphokine-activated killer cells in the treatment of patients with advanced renal cell carcinoma. Cancer 1995; 76(5):824-832.
(19) Rosenberg S A, Lotze M T, Yang J C, Topalian S L, Chang A E, Schwartzentruber D J et al. Prospective randomized trial of high-dose interleukin-2 alone or in conjunction with lymphokine-activated killer cells for the treatment of patients with advanced cancer. J Natl Cancer Inst 1993; 85(8):622-632.
(20) Parmiani G. An explanation of the variable clinical response to interleukin 2 and LAK cells. Immunol Today 1990; 11(4):113-115.
(21) Cabrera T, Angustias F M, Sierra A, Garrido A, Herruzo A, Escobedo A et al. High frequency of altered HLA class I phenotypes in invasive breast carcinomas. Hum Immunol 1996; 50(2):127-134.
(22) Cabrera T, Salinero J, Fernandez M A, Garrido A, Esquivias J, Garrido F. High frequency of altered HLA class I phenotypes in laryngeal carcinomas. Hum Immunol 2000; 61(5):499-506.
(23) Tongio M M. 12th International Histocompatibility Workshop HLA class I monoclonal antibodies study. In: Charron D, editor. HLA: Genetic diversity of HLA. Functional and medical Implication. Charron, D., 1997: 7-12.
(24) Bignon J D. HLA DNA class II typing by PCR-SSOP: 12th International Histocompatibility Workshop experience. In: Charron D, editor. HLA: Genetic diversity of

(25) Norgaard L. A mRNA based SBT protocol for typing of HLA-A locus alleles. In: Charron D, editor. HLA: Genetic diversity of HLA. Functional and medical Implication. EDK Medical and Scientific International Publisher, 1997: 254-256.
(26) Lardy N M. One dimensional iso-electric focusing (1D-IEF) of HLA class I variants: 12th International Histocompatibility Workshop experience. In: Charron D, editor. HLA: Genetic diversity of HLA. Functional and medical Implication. EDK Medical and Scientific International Publisher, 1997: 18-20.
(27) Schendel D J, Wank R, Dupont B. Standardization of the human in vitro cell-mediated lympholysis technique. Tissue Antigens 1979; 13(2):112-120.
(28) Browning M J, Madrigal J A, Krausa P, Kowalski H, Allsopp C E, Little A M et al. The HLA-A, B, C genotype of the class I negative cell line Daudi reveals novel HLA-A and -B alleles. Tissue Antigens 1995; 45(3):177-187.
(29) Taniguchi K, Petersson M, Hoglund P, Kiessling R, Klein G, Karre K. Interferon gamma induces lung colonization by intravenously inoculated B16 melanoma cells in parallel with enhanced expression of class I major histocompatibility complex antigens. Proc Natl Acad Sci USA 1987; 84(10):3405-3409.
(30) Jabrane-Ferrat N, Calvo F, Faille A, Lagabrielle J F, Boisson N, Quillet A et al. Recombinant gamma interferon provokes resistance of human breast cancer cells to spontaneous and IL-2 activated non-MHC restricted cytotoxicity. Br J Cancer 1990; 61(4):558-562.
(31) Schendel D J, Falk C S, Nossner E, Maget B, Kressenstein S, Urlinger S et al. Gene transfer of human interferon gamma complementary DNA into a renal cell carcinoma line enhances MHC-restricted cytotoxic T lymphocyte recognition but suppresses non-MHC-restricted effector cell activity. Gene Ther 2000; 7(11):950-959.
(32) Schendel D J, Gansbacher B, Oberneder R, Kriegmair M, Hofstetter A, Riethmuller G et al. Tumor-specific lysis of human renal cell carcinomas by tumor-infiltrating lymphocytes. I. HLA-A2-restricted recognition of autologous and allogeneic tumor lines. J Immunol 1993; 151(8):4209-4220.
(33) Giacomini P, Beretta A, Nicotra M R, Ciccarelli G, Martayan A, Cerboni C et al. HLA-C heavy chains free of beta2-microglobulin: distribution in normal tissues and neoplastic lesions of non-lymphoid origin and interferon-gamma responsiveness. Tissue Antigens 1997; 50(6):555-566.
(34) Maier S, Grzeschik M, Weiss E H, Ulbrecht M. Implications of HLA-E allele expression and different HLA-E ligand diversity for the regulation of NK cells [In Process Citation]. Hum Immunol 2000; 61(11):1059-1065.
(35) Schendel D J, Maget B, Falk C S, Wank R. Human CD8+ T lymphocytes. In: Levkovits I, editor. the Immunology Methods Manual. London: Academic Press, 1997: 670-690.
(36) Shimizu Y, DeMars R. Production of human cells expressing individual transferred HLA-A, -B, -C genes using an HLA-A, -B, -C null human cell line. J Immunol 1989; 142(9):3320-3328.
(37) Gastl G, Finstad C L, Guarini A, Bosl G, Gilboa E, Bander N H et al. Retroviral vector-mediated lymphokine gene transfer into human renal cancer cells. Cancer Res 1992; 52(22):6229-6236.

TABLE 1

Phenotype analysis of LAK populations

| | $CD3^- CD56^+$ | $CD3^+ CD56^+$ | $CD3^+ CD4^+$ | $CD3^+ CD8^+$ |
|---|---|---|---|---|
| LAK-26 | 1 ± 0* | 9 ± 2 | 52 ± 5 | 50 ± 0 |
| LAK-53 | 5° | 6 | 63 | 33 |
| LAK-CP176 | 3 ± 2 | 17 ± 7 | 19 ± 6 | 78 ± 7 |
| LAK-CP41 | 6 ± 2 | 14 ± 10 | 46 ± 15 | 46 ± 12 |

*The data represent mean percentages (with standard deviations) of positive cells derived from four or more experiments.
°Only two experiments could be performed due to limited growth.

TABLE 2

Reversal of MHC class I-mediated inhibition by αMHC class I mab

| Effector cells | E:T* | mab° | Target Cells | | | | | |
|---|---|---|---|---|---|---|---|---|
| | | | RCC-26 | +IFNγ | RCC-26VC | +IFNγ | endoγ1 | endoγ2 |
| LAK-26 | 20:1 | isotype | 20 | 15 | 25 | 19 | 8 | 7 |
| | | α class I | 24 | 30 | 32 | 31 | 15 | 16 |
| LAK-CP41 | 20:1 | isotype | 9 | 4 | nt^ | nt | 4 | 4 |
| | | α class I | 26 | 15 | nt | nt | 20 | 21 |
| B.3 NK | 20:1 | isotype | 59 | 15 | 33 | 15 | 8 | 13 |
| | | α class I | 69 | 55 | 46 | 46 | 41 | 42 |

*effector to target cell ratio
°mab concentrations: 10 μg/ml
^not tested

TABLE 3

Analysis of inhibitory receptor expression on LAK populations

| | NK cell markers | | | | | | | |
|---|---|---|---|---|---|---|---|---|
| | p58.1 | | p58.2 | | NKB1 | | CD94 | |
| | $CD3^+$ | $CD3^-$ | $CD3^+$ | $CD3^-$ | $CD3^+$ | $CD3^-$ | $CD3^+$ | $CD3^-$ |
| LAK-26 | 0 ± 0* | 0 ± 0 | 1 ± 1 | 1 ± 1 | 0 ± 0 | 0 ± 0 | 7 ± 7 | 7 ± 8 |
| LAK-CP176 | 0 ± 0 | 0 ± 0 | 1 ± 0 | 1 ± 1 | 0 ± 0 | 0 ± 0 | 6 ± 2 | 3 ± 2 |

TABLE 3-continued

Analysis of inhibitory receptor expression on LAK populations

| | NK cell markers | | | | | | | |
|---|---|---|---|---|---|---|---|---|
| | p58.1 | | p58.2 | | NKB1 | | CD94 | |
| | CD3+ | CD3− | CD3+ | CD3− | CD3+ | CD3− | CD3+ | CD3− |
| LAK-CP41 | 0 ± 0 | 0 ± 0 | 1 ± 0 | 1 ± 1 | 0 ± 0 | 0 ± 0 | 3 ± 1 | 5 ± 2 |
| B.3NK | 0 ± 0 | 0 ± 0 | 0 ± 0 | 95 ± 4 | 0 ± 0 | 0 ± 0 | 0 ± 0 | 85 ± 15° |

*The data represent mean percentages (with standard deviations) of positive cells derived from four or more experiments.
°These CD94 molecules are associated with an activating NKG2C molecule.

What is claimed is:

1. A therapeutic composition comprising:
   (i) non-MHC-restricted T cells in combination with either:
      a) MHC-restricted T cells; or
      b) a therapeutic agent for inducing immune responses of MHC-restricted T cells; and
   (ii) a pharmaceutically acceptable carrier,
   wherein the composition comprising non-MHC-restricted T cells comprises Lymphokine Activated Killer T cells (LAK-T cells) depleted of natural killer cells.

2. The therapeutic composition of claim 1, wherein the therapeutic agent for inducing MHC-restricted T-cell responses is a genetically engineered tumor cell.

3. The therapeutic composition of claim 1, wherein the therapeutic agent for inducing MHC-restricted T-cell responses is a vaccine comprising tumor cells or dendritic cells.

4. The pharmaceutical composition of claim 1, wherein the therapeutic agent for inducing immune responses of MHC-restricted T cells is selected from the group consisting of a genetically engineered tumor cell and a vaccine comprising tumor cells or dendritic cells.

5. A method of therapeutically treating a patient suffering from a tumor disease, said method comprising administering to said patient a therapeutically effective dosage of the therapeutic composition of claim 1.

6. The method of claim 5, wherein tumors, which show a low, missing or aberrant expression of MHC class Ia or Ib molecules, are treated.

7. The method of claim 6, wherein the tumors show a low, missing or aberrant expression of HLA-C and/or HLA-E molecules.

8. The method of claim 5, wherein a mammal is treated.

9. The method of claim 5, wherein a human is treated.

10. The method of claim 5, wherein the tumor disease comprises a tumor selected from the group consisting of a colon carcinoma, a breast carcinoma, a prostate carcinoma, a renal cell carcinoma (RCC), and a melanoma.

11. A method of therapeutically treating a patient suffering from a tumor disease comprising administering to a patient having a tumor disease exhibiting a low, missing or aberrant expression of MHC class Ia or Ib molecules and a low, missing or aberrant expression of HLA-C and/or HLA-E molecules a therapeutically effective dosage of activated non-MHC-restricted T cells and/or Natural Killer (NK) cells in combination with either:
   (a) MHC-restricted T cells; or
   b) a therapeutic agent for inducing immune responses of MHC-restricted T cells.

12. The method of claim 11, comprising administering non MHC-restricted T-cells and/or NK cells prior to administering MHC-restricted T-cells or therapeutic agents for inducing MHC-restricted T cell responses.

13. The method of claim 11, comprising administering non MHC-restricted T-cells and/or NK cells simultaneously with administering MHC-restricted T-cells or therapeutic agents for inducing MHC-restricted T cell responses.

14. The method of claim 11, comprising administering non MHC-restricted T-cells and/or NK cells subsequent to administering MHC-restricted T-cells or therapeutic agents for inducing MHC-restricted T cell responses.

15. The method of claim 11, further comprising the step of initially determining the MHC class I expression in the tumor.

16. The method of claim 11, wherein the non MHC-restricted T-cells and/or NK cells consist of LAK cells.

17. The method of claim 11, wherein the tumor disease comprises a tumor selected from the group consisting of a colon carcinoma, a breast carcinoma, a prostate carcinoma, a renal cell carcinoma (RCC), and a melanoma.

18. A kit comprising non-MHC-restricted T cells in combination with either:
   a) MHC-restricted T cells; or
   b) a therapeutic agent for inducing immune responses of MHC-restricted T cells; wherein the non-MHC-restricted T cells comprise Lymphokine Activated Killer T cells (LAK-T cells) depleted of natural killer cells.

19. The kit of claim 18, wherein the therapeutic agent for inducing MHC-restricted T-cell responses is a genetically engineered tumor cell.

20. The kit of claim 18, wherein the therapeutic agent for inducing MHC-restricted T-cell responses is a vaccine comprising tumor cells or dendritic cells.

* * * * *